Patent Number: 4,502,508
Date of Patent: Mar. 5, 1985

United States Patent [19]
Lester

[54] SPOOL VALVE FOR CONNECTING AN OUTPUT TO ONE OF TWO INPUTS

[75] Inventor: Graham G. Lester, Folkestone, England

[73] Assignee: Smiths Industries Public Limited Company, London, England

[21] Appl. No.: 477,551

[22] Filed: Mar. 21, 1983

[30] Foreign Application Priority Data

Mar. 29, 1982 [GB] United Kingdom ............... 8209172

[51] Int. Cl.$^3$ ............................................. E03B 3/00
[52] U.S. Cl. ............................ 137/625.69; 137/625.48
[58] Field of Search .................. 137/625.69, 625.48, 137/625.47

[56] References Cited

U.S. PATENT DOCUMENTS

| Re. 25,251 | 10/1962 | Quail | 137/625.69 |
|---|---|---|---|
| 318,000 | 5/1885 | Jefferies | 137/625.69 |
| 2,094,926 | 10/1937 | Nutter et al. | 137/625.69 |
| 3,131,722 | 5/1964 | Abbott et al. | 137/625.69 |
| 3,661,182 | 5/1972 | Loveless | 137/625.48 |
| 3,916,948 | 11/1975 | Benjamin | 137/625.48 |
| 3,951,166 | 4/1976 | Whitener | 137/625.69 |
| 4,273,027 | 6/1981 | Reinhard et al. | 137/625.69 |

Primary Examiner—Edward G. Favors
Assistant Examiner—Steven E. Warner
Attorney, Agent, or Firm—Pollock, Vande Sande and Priddy

[57] ABSTRACT

A valve has a tubular housing with two inlets spaced apart along its length, and a single outlet intermediate the inlets on the opposite side of the housing. One end of the housing is closed, its other end being open. The first inlet, close to the open end, is connected to a source of reduced pressure; the second inlet opening, close to the closed end, is connected to a source of raised pressure. A valve member is displaceable along the housing, being urged to the open end by a spring. First, second and third dished flanges are mounted coaxially on the valve member. The three flanges are spaced such that the outlet is connected to the second inlet when the first flange is located between the outlet and the first inlet, and the other two flanges are located between the open end of the housing and the second inlet. The outlet is connected to the first inlet when the valve member is positioned with the second flange between the second inlet and the outlet, and the first flange between the first inlet and the closed end of the housing. The valve member can be positioned such that the outlet is isolated from both inlets, when the second flange is located between the outlet and the second inlet, and the first flange is located between the outlet and the first inlet. The orientation of the flanges is such that pressure within the valve improves the seal of the flanges with the housing.

6 Claims, 7 Drawing Figures

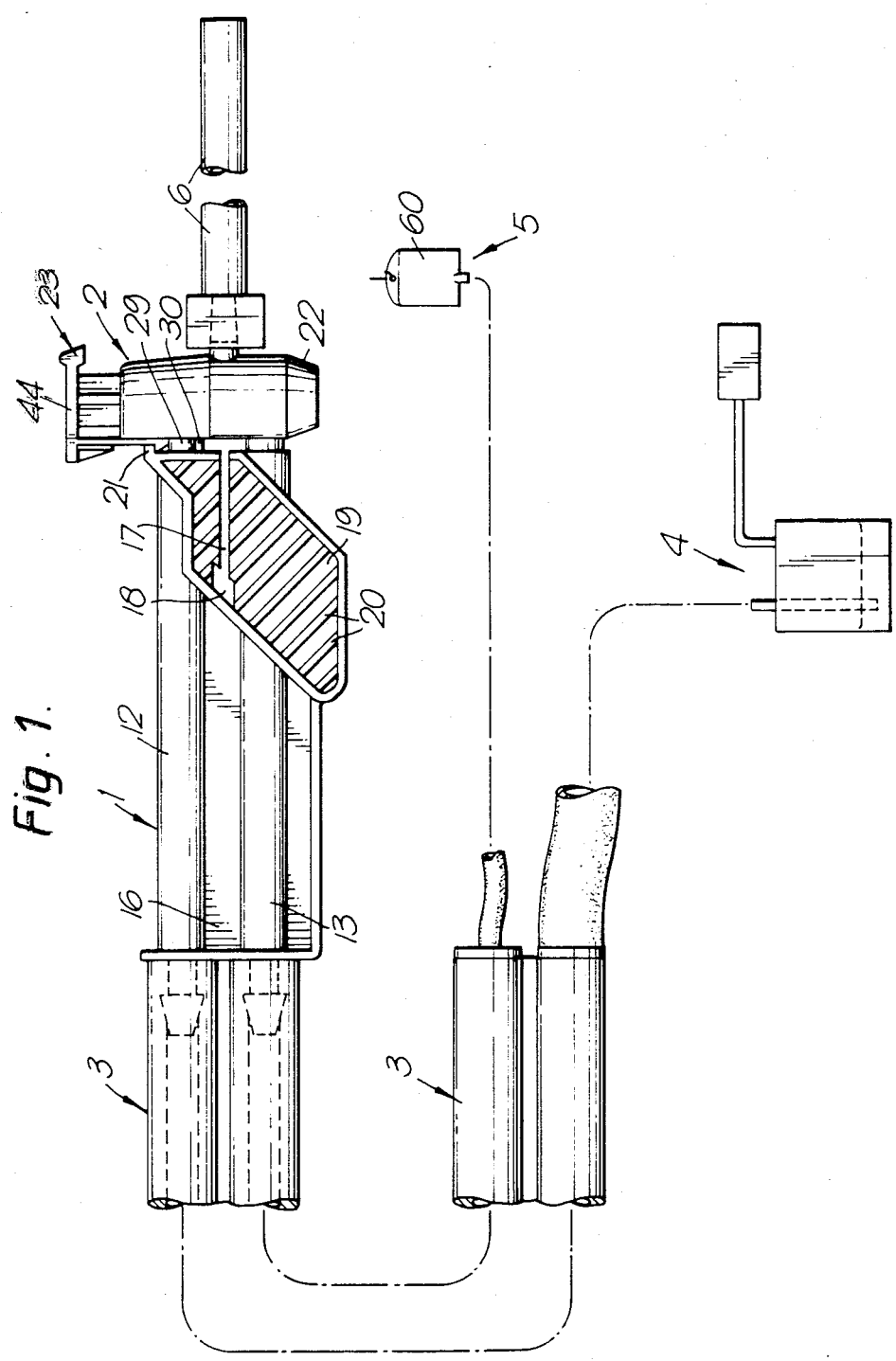

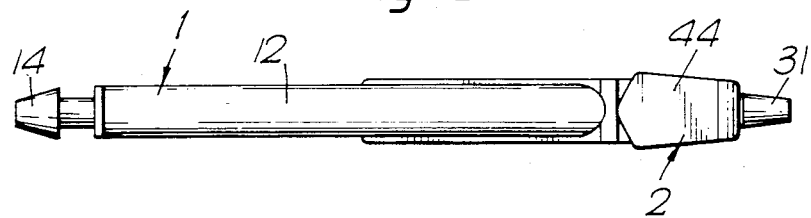
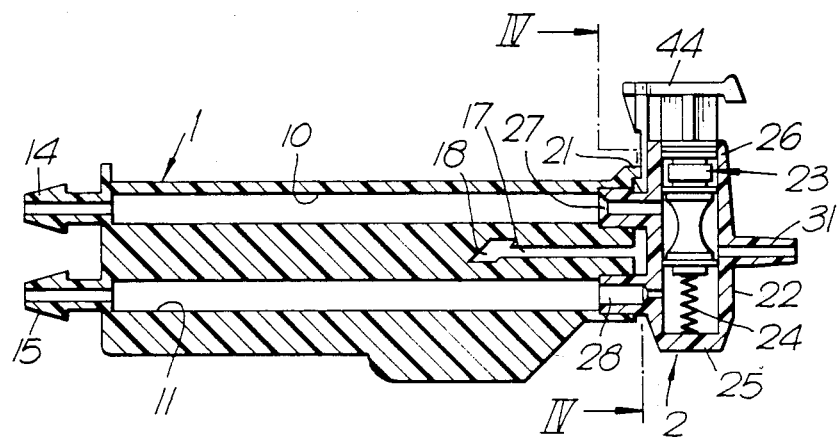
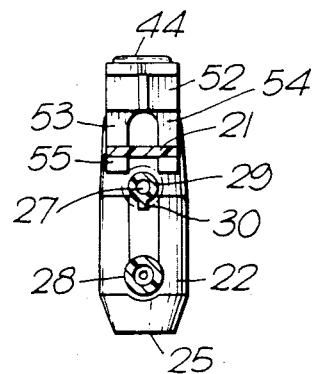

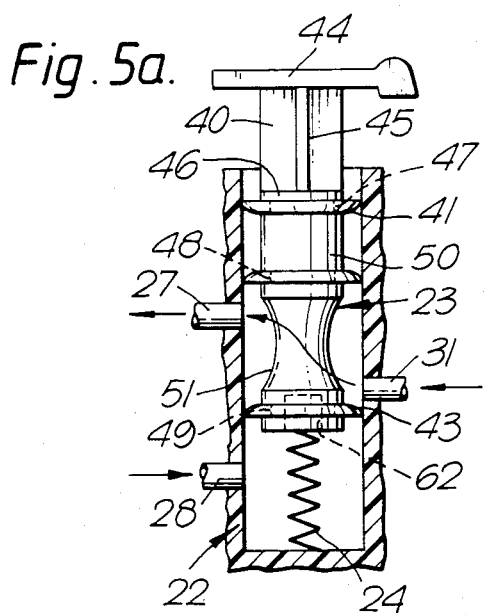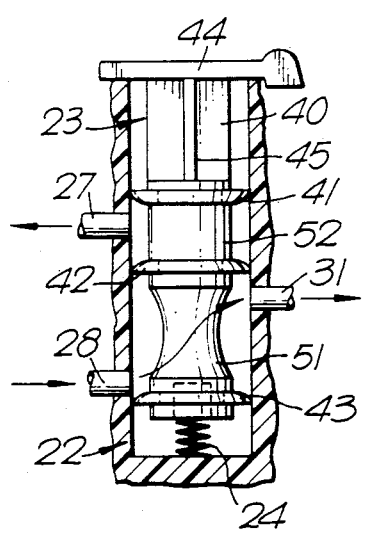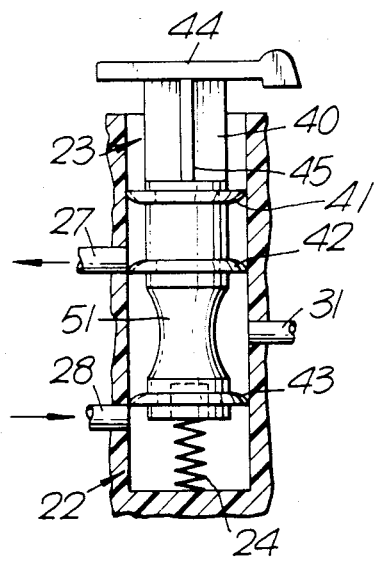

SPOOL VALVE FOR CONNECTING AN OUTPUT TO ONE OF TWO INPUTS

BACKGROUND OF THE INVENTION

This invention relates to valve assemblies.

The invention is more particularly concerned with spool valve assemblies of the kind for making interconnection of an outlet with one of two or more inlets at different pressures.

Spool valves have an outer housing provided with inlet and outlet ports in its wall at locations spaced along its length. A valve member is movable along the length of the housing and has several annular sealing flanges that slide over the wall to provide a fluid-tight seal. By appropriately positioning the sealing flanges fluid can be directed around the valve body between the desired ports.

The problem with such valves is that they are prone to leakage between the sealing flanges and the wall of the housing. This can be an especial problem where fluids are supplied at high pressure or where the sealing flanges have become worn or otherwise degraded after prolonged use.

BRIEF SUMMARY OF THE INVENTION

It is an object of the present invention to provide a valve assembly that can be used substantially to alleviate the above-mentioned disadvantage.

According to one aspect of the present invention there is provided a valve assembly including a housing and a valve member, the housing having a bore with first and second openings in its wall which are for connection respectively to a source of raised pressure and reduced pressure, and a third opening which is arranged for connection with said first or second openings by appropriate positioning of said valve member, wherein said valve member has three sealing flanges that contact the wall of the housing to form a seal therewith, wherein said flanges are located such that at least one of said first or second openings is sealed from said third opening at any position of said valve member, wherein said flanges are of substantially dished shape, and wherein the flange or flanges sealing said first or second openings from said third opening are oriented such that the pressure applied to the valve assembly tends to urge said flange or flanges into closer contact with the wall of the housing.

In this way, the pressure supplied to the valve assembly acts to improve the sealing property of the flanges.

The bore of the housing may be open at one end and closed at the other end, the first opening being located towards the closed end of the housing and the second opening being located towards the open end of the housing. The assembly may be arranged such that the first opening is connected to the third opening when the valve member is positioned such that the first and third openings are both located intermediate first and second adjacent ones of said flanges, and the second opening is connected to the third opening when the valve member is positioned such that the second and third openings are both located intermediate the first and second adjacent ones of the flanges. The openings and the flanges may be located such that the valve member can be positioned to isolate the third opening from both the first and second openings. The openings and the flanges may be located such that the third opening can be isolated from both the first and second openings by positioning the valve member such that a first of the flanges is located intermediate the first opening and the third opening that a second of the flanges is located intermediate the second opening and the third opening, and that a third of the flanges is located on the side of the second opening remote from the third opening. The first and third of the flanges may be located at opposite ends of the valve member and may be dished such that their outer edges are located further from one another than their inner edges. The first flange may be located at the end of the valve member close to the first opening, and the second flange may be located intermediate the first and third flanges and have an outer edge that is dished towards the first flange.

A medical suction irrigator including a valve according to the present invention, will now be described, by way of example, with reference to the following drawings.

BRIEF DESCRIPTION OF THE DRAWINGS

FIG. 1 is a side elevation view of the suction irrigator;

FIG. 2 is a plan view of the suction irrigator of FIG. 1;

FIG. 3 shows the suction irrigator in section;

FIG. 4 is a sectional view along the line IV—IV of FIG. 3; and

FIGS. 5a, 5b and 5c show the valve of the suction irrigator in greater detail, in three different positions.

DETAILED DESCRIPTION

With reference to FIGS. 1 to 3, the suction irrigator is in two parts, namely, a handle 1 and a valve assembly 2. The suction-irrigation system comprises double tubing 3 which connects the suction irrigator with a suction source 4 and a source of irrigation fluid 5. A probe 6 is fitted to the valve assembly 2 which is operable to connect the probe to the suction source 4 or the source of irrigation fluid 5.

With reference now especially to FIG. 3, the handle 1 is a unitary assembly of a rigid plastics material and may be made as a two-part molding. The handle 1 is of generally rectangular shape and has two cylindrical bores 10 and 11 which run along the handle from its rear end to its forward end through tubular formations 12 and 13. At their rear ends the bores 10 and 11 are terminated with tapered spigots 14 and 15 which are received within respective bores at the forward end of the double tubing 3. The tubular formations 12 and 13 are linked by a central flat land 16 that extends along the length of the handle 1. At its forward end, the land 16 is formed with a slit 17 that extends parallel to the tubular formations 12 and 13 and that is slightly enlarged at its rear end 18. A lozengeshape grip portion 19 (FIG. 1) is formed at the forward end of the handle 1 by raised ribs 20 extending across the tubular formations 12 and 13 and the land 16. Above the forward end of the upper tubular formation 12 the handle is formed with a small lip 21, the purpose of which will become apparent later.

The valve assembly 2 is shown most clearly in FIGS. 3 and 5a to 5c. The assembly comprises three parts: an outer housing 22, a valve member 23, and a spring 24. The housing 22 is a precision plastics injection molding of generally cylindrical shape, having a closed lower end 25 and an open upper end 26. On one side of the housing 22 are provided two inlet ports 27 and 28 spaced apart along the housing, the lower port 28 being arranged to fit within the forward end of the irrigation fluid bore 11 while the upper port 27 is similarly received within the end of the suction bore 10. Both ports 27 and 28 are provided by short parallel conduits projecting from the housing 22, the upper conduit being waisted close to the body of the housing to form a portion 29 of reduced external diameter that is reinforced by a web 30 extending along its lower edge. From the other side of the housing 22 there extends an outlet conduit or port 31 which is positioned between the two inlet ports and parallel with them. The outer surface of the outlet conduit is formed with a luer-taper for receiving the probe 6.

The three ports 27,28 and 31 communicate with the interior of the body of the housing 22 which is accurately dimensioned and of cylindrical shape. The interior of the housing 22 contains the valve member 23 and the spring 24, the spring bearing on the lower end 25 of the housing and acting to urge the valve member 23 upwardly, transversely of the ports 27,28 and 31.

The valve member 23 has a rigid plastics body or stem 40 on which are mounted three resilient, elastomeric sealing flanges 41,42 and 43 that contact the internal surface of the housing 22. At its upper end, the stem 40 has a flat horizontal plate 44 on which the user places his finger or thumb to displace the valve member against the action of the spring 24. Beneath the plate 44 the stem has a short portion 45 of cruciform shape that terminates in a flat circular plate 46. Below the plate 46 the valve stem is of circular cross-section and is provided with three annular grooves 47,48 and 49 in which the sealing flanges 41 to 43 respectively are mounted. The flanges 41 to 43 are each dished such that the outer edges of the middle and lower flanges 42 and 43 are normally below their inner edges, that is, are convex when viewed from above; the upper flange 41 is mounted the other way up so that its outer edge is above its inner edge, thereby being concave when viewed from above. The upper flange 41 and the middle flange 42 are separated by a short cylindrical section 50 of the valve stem 40. The middle flange 42 and the lower flange 43 are separated by a waisted section 51 of concave profile. At its lower end the stem 40 has a central recess 62 in which the upper end of the steel spring 24 is received.

At the other end of the valve stem 40, the top plate 44 is provided with a downwardly-extending catch member 52 of generally inverted 'U'-shape (FIG. 4). When the stem 40 is located in the housing 22, the catch member 52 extends between the outside of the housing and the forward end of the handle 1. The catch member 52 has two arms 53 and 54 which extend down opposite sides of the port 27 astride its portion 29 of reduced diameter. On their rear surfaces the arms 53 and 54 are both provided with a raised tooth 55 that is arranged to engage the lower edge of the lip 21 so as thereby to limit upward travel of the valve member 23.

The suction irrigator is readily assembled by joining the valve housing 22 with the handle 1. In this respect, an adhesive or solvent may be applied to the outer surface of the ports 27 and 28, or to the forward end of the bores 10 and 11 so that the two parts are securely joined. The valve member 23 and spring 24 may be assembled before or after the housing 22 has been joined to the handle 1 since the resilience of the catch member 52 enables it to be pushed downwardly over the lip 21 to snap into position.

The suction irrigator would normally be used with the removable probe 6. The probe 6 is a single-bore tube that is formed at its rear end with a Luer-tapered connector that can be push fitted over the outlet port 31. The probe 6 may be different shapes and sizes according to the use to which it is to be put. Preferably, the internal diameter of the probe is less than that of the port 31 so that any blockage that might occur takes place within the probe. In this way, the probe can be readily replaced if the blockage cannot be removed.

In its natural position, the valve stem 40 is urged to its upper limit of its travel by the spring 24 until the catch member 52 engages the lip 21. This position is shown in FIG. 5a and it can be seen that the lower flange 43 on the valve stem is situated intermediate the outlet port 31 and the irrigation port 28 thereby effectively sealing the irrigation port from the outlet port. The middle flange 42 is situated just above the suction port 27 so that fluid is enabled to flow between the outlet port 31 and the suction port around the waisted section 51 of the valve stem. In this position therefore suction is applied to the outlet port 31 and the probe 6.

When the valve member 23 is depressed fully by pushing on the plate 44, as shown in FIG. 5b, the middle flange 42 moves to a position intermediate the outlet port 31 and the suction port 27 whereas the lower flange 43 lies just below the irrigation port 28. In this position therefore the irrigating fluid is free to flow from the port 28 to the outlet port 31, and from there to the probe 6.

It is also possible to position the valve member 23 so that the outlet port 31 is sealed from both the irrigation and suction sources. This position is shown in FIG. 5c and relies on positioning the middle flange 42 just below the suction port 27, and the lower flange just above the irrigation port 28.

The sealing flanges 41 to 43 are oriented so as to improve the seal with the wall of the housing 22; more particularly, they are arranged so that the pressure exerted on either side of each flange operates to urge them into closer contact with the wall of the housing. In the suction position, shown in FIG. 5a, the pressure of irrigating fluid supplied to the lower port 28 will force the outer edge of the lower flange 43 upwards into a more flat shape. Flattening the flange 43 will tend to give it a greater external diameter thereby bringing its outer edge into closer contact with the wall of the housing 22. The suction applied to the upper port 27 will also tend to flatten the lower flange 43 but because the suction port 27 is open to atmosphere via the outlet port 31, the pressure above the lower flange 43 will be substantially the same as atmospheric pressure. The suction will tend to make the seal provided by the middle flange 42 less effective but any leakage past this flange will be stopped by the upper flange 41 which is oriented such as to give an improved seal when suction is applied beneath it.

In the irrigation position, shown in FIG. 5b, the lower flange 43 moves below the irrigation port 28 and trapped fluid beneath the flange, in the lower part of the housing 22 will tend to force the flange into closer contact with the housing. The effectiveness of the seal provided by the lower flange 43 is, however, not so important in the irrigation mode since any leakage past the flange will be contained within the housing. In this position, the suction port 27 is sealed off below by the middle flange 42 and above by the upper flange 41. These flanges 41 and 42 both present convex surfaces to the port 27 so that the reduced pressure in the chamber defined between the two flanges tends to deform them into closer contact with the housing 22.

In the neutral position shown in FIG. 5c, the suction conduit 27 is also sealed between the upper and middle flanges 41 and 42, while the lower flange is situated just above the irrigation conduit 28 so that it seals the irrigation conduit in the same manner as in the suction mode.

In the suction mode, the user simply places the tip of the probe 6 close to the material to be removed and this is drawn through the probe and the suction bore 10 into the appropriate bore of the double tubing 3. To irrigate, the user depresses the valve member 23 to its fullest extent and the irrigation fluid—which may be supplied from a suspended bag 60 of saline solution—passes out of the tip of the probe. Placement of the probe tip can, in some circumstances, be made easier by partially depressing the valve member to the neutral position shown in FIG. 5c so that the outlet port 31 is sealed off.

The suction irrigator can be used for picking up and placing material such as tissue. To do this, the equipment is placed in the suction mode and the tip of the probe 6 is placed in contact with the material to be transferred, thereby causing it to be attracted to the probe. The material can then be lifted to a new location. When the material is correctly located, the valve member 23 is depressed so that the equipment is switched to the irrigating mode thereby causing the material to be forced off the end of the probe 6 by the pressure of fluid within it. Minor blockages that might occur in the suction mode can be cleared by changing to the irrigation mode so that the obstruction is forced out of the probe 6.

Because only a single bore outlet conduit and probe are used, this can be narrower than previous double conduit arrangements thereby making the equipment easier to use in restricted places.

The valve assembly of the present invention could be used in other applications and is not confined to medical suction irrigators. Different numbers and arrangements of inlet and outlet ports, and flanges could also be used.

What I claim is:

1. A valve assembly having a tubular housing, said housing being closed at one end, and said housing having a wall, a first opening in said wall close to and spaced from said closed end, a second opening in said wall spaced from said first opening away from said closed end, one of said first and second openings being adapted for connection to a source of raised pressure and the other of said first and second openings being adapted for connection to a source of reduced pressure, and a third opening in said wall located intermediate said first and second openings; the valve assembly including a valve member that is displaceable along the tubular housing, said valve member having three sealing flanges which extend outwards of said valve member in spaced relation to one another and in sealing engagement with said wall of said tubular housing, the first one of said sealing flanges being located closest to the closed end of said housing, the second one of said sealing flanges being located furthest from said closed end of said housing, and the third one of said sealing flanges being located intermediate said first and second sealing flanges, the relative disposition of said three sealing flanges and said three openings being such that, in a first position of the valve member, the first flange is located intermediate the first and third openings, with the second and third flanges being both located on a side of the second opening remote from said third opening such that said third opening is connected to said second opening and is isolated from said first opening, and in a second position of the valve member the first flange is located intermediate said first opening and the closed end of said housing, with the third flange being located intermediate the second and third openings and the second flange being located on the opposite side of said second opening such that said third opening is connected to said first opening and is isolated from said second opening, each of said flanges being of dished shape, said first and third flanges being dished in the same sense and said second flange being dished in the opposite sense such that pressure applied to the valve assembly tends to urge the second flange into closer contact with the wall of the housing at both of said first and second positions of said valve element and tends to urge the first and third flanges into closer contact with the wall of the housing when they lie intermediate said third opening and said first or second openings, respectively.

2. A valve assembly according to claim 1 wherein said first opening is adapted for connection to the source of raised pressure and said second opening is adapted for connection to the source of reduced pressure, said first and third flanges being dished with their outer edges closer to the closed end of the housing than their inner edges, and said second flange being dished with its outer edge further from the closed end of the housing than its inner edge.

3. A valve assembly according to claim 1 wherein said openings and said flanges are located such that the valve member is displaceable to a third position in which said third opening is isolated from both said first and second openings.

4. A valve assembly according to claim 3 wherein said third opening is isolated from both said first and second openings when said valve member in said third position is so positioned that said first flange is located intermediate said first opening and said third opening, said third flange is located intermediate said second opening and said third opening, and said second flange is located on a side of said second opening remote from said third opening.

5. A valve assembly according to claim 1, wherein said valve member includes a valve body of substantially cylindrical shape, and wherein said valve body is waisted to a reduced diameter between said first and third flanges.

6. A valve assembly according to claim 1 including a spring member, and means mounting said spring member between said valve member and said housing such as to urge said valve member out of said housing.

* * * * *